(12) United States Patent
Facon et al.

(10) Patent No.: US 6,228,606 B1
(45) Date of Patent: May 8, 2001

(54) CULTURE MEDIUM FOR DETECTING PATHOGENIC BACTERIA OF THE GENUS LISTERIA AND METHOD FOR IDENTIFYING SAID BACTERIA

(75) Inventors: Jean-Pierre Facon, Fleurbaix; Frederic Simon, Terdeghem, both of (FR)

(73) Assignee: Pasteur Sanofi Diagnostics, Marnes la Coquette (FR)

( * ) Notice: Subject to any disclaimer, the term of this patent is extended or adjusted under 35 U.S.C. 154(b) by 0 days.

(21) Appl. No.: 09/462,100

(22) PCT Filed: Jul. 10, 1998

(86) PCT No.: PCT/FR98/01516

§ 371 Date: Jun. 22, 2000

§ 102(e) Date: Jun. 22, 2000

(87) PCT Pub. No.: WO99/04032

PCT Pub. Date: Jan. 28, 1999

(30) Foreign Application Priority Data

Jul. 15, 1997 (FR) .................................................. 97 08960

(51) Int. Cl.$^7$ .............................. C12Q 1/04; C12Q 1/02; C12Q 1/00
(52) U.S. Cl. ................................ 435/34; 435/18; 435/29; 435/4; 435/404; 435/405
(58) Field of Search .................................... 435/34, 18, 29, 435/4, 404, 405

(56) References Cited

U.S. PATENT DOCUMENTS 6,051,391 * 4/2000 Schabert et al. ....................... 435/21

FOREIGN PATENT DOCUMENTS 0326062  1/1989 (EP) .
049680 A1  1/1992 (EP) .

OTHER PUBLICATIONS

"Purification and Characterization of *Listeria Motocytogenes* Phosphatidylinositol–Specific Phospholipase C," *Infection and Immun.*60, 10 1992. pp. 4059–4067.

"Identification of Phosphatidylinositol–Specific Phospholipase C Activity In *Listeria Monocytogenes*: A Novel Type of Virulence Factor?" *Molecular Microbiology* 5, (2) 1991. pp. 367–372.

Phosphatidylinositol–Specific Phospholipase C Activity As A Marker To Distinguish Between Pathogenic And Non-pathogenic Listeria Species *Appl. Environ. Microbiol,* 57, (9) 1991. pp. 2666–2670.

* cited by examiner

Primary Examiner—Louise N. Leary
(74) Attorney, Agent, or Firm—Jacobson, Price, Holman & Stern, PLLC

(57) ABSTRACT

The present invention relates to a nutritive agar culture medium allowing the direct identification of pathogenic bacteria of the genus Listeria, said medium comprising a chromogenic synthetic substrate specifically cleaved by the phospholipase C specific of phosphatidylinositol (PIPLC).

22 Claims, No Drawings

CULTURE MEDIUM FOR DETECTING PATHOGENIC BACTERIA OF THE GENUS LISTERIA AND METHOD FOR IDENTIFYING SAID BACTERIA

The present invention relates to a culture medium allowing the investigation, the isolation, the counting and the direct identification of pathogenic bacteria of the genus Listeria as well as a method employing this medium.

The isolation and the identification of the bacterium *Listeria monocytogenes* is a major problem in the monitoring of agrifood hygiene and of medical bacteriology. Among the bacteria of the genus Listeria spp only the species *monocytogenes* is known to be pathogenic for man. The other species of Listeria are not pathogenic or are pathogenic only for animals. This is the case, especially, for *Listeria ivanovii*. It is additionally known that is possible to inhibit the growth of *Listeria monocytogenes* by using bacteriocins. For example, the Patent Application EP 326 062 describes a method for inhibition of *Listeria monocytogenes* which employs a bacteriocin originating from *Pediococcus acidilactici*.

The route of contamination by *Listeria monocytogenes* is most often of food origin. Thus, it is necessary to provide for the detection of *Listeria monocytogenes* all along the agrifood pathway, from raw materials passing through the environment of production facilities up to the finished product intended for consumption.

Within the context of diagnosis of bacterial conditions in man, it is likewise important to distinguish *Listeria monocytogenes* from among the other bacteria of the genus Listeria spp. which are not pathogens.

The detection and the isolation of Listeria spp. are conventionally carried out using selective culture media. The Oxford (Curtis et al., *Lett. Appl. Microbiol.* (1989), 8, pp. 85–98) and Palcam (Van Netten et al., *J. Food Microbiol.* (1988), 6, pp. 187–188) selective media are the most currently used. These media allow the detection of all the species of the genus Listeria spp. Thus, the typical colonies observed must be subjected to supplementary identification tests, such as microscopic and/or biochemical and/or immunological and/or genetic tests, so as to establish membership of the *monocytogenes* species. However, the supplementary manipulations necessary for the identification of *Listeria monocytogenes* increase the length and the cost of the analyses. They require a vast number of reagents and the use of qualified personnel. In addition, the withdrawal of the colonies subjected to the identification being uncertain, the supplementary manipulations are often a source of error or at least the cause of lower precision and reliability. This is the case especially when the colonies of *Listeria monocytogenes* on the isolation medium are very minor with respect to the colonies formed by the other species of Listeria.

The Patent Application EP 496 680 describes a bacteriological analysis method to differentiate *Listeria monocytogenes* from other bacteria of the genus Listeria spp.

According to this method, an identification medium is used comprising a chromogenic or fluorogenic substrate capable of being hydrolysed by glycine aminopeptidase. The medium used can likewise possibly contain a fermentation substrate and/or a reducible substrate and/or a substrate which is hydrolysable enzymatically (such as the substrate of α-mannosidase) whose chemical transformation allows the species Listeria present in the sample to be analysed to be characterized.

It is additionally known that it is possible to discriminate pathogenic species of *Listeria, Listeria monocytogenes* and *Listeria ivanovii* from other Listeria by demonstrating the specific phosphatidylinositol activity of specific phospholipase C of phosphatidylinositol (PIPLC).

In fact, it has been shown that PIPLC is secreted into the culture medium of pathogenic species of the genus Listeria such as *Listeria monocytogenes* and *Listeria invanovii* (Leimeister-Wächter et al., *Mol. Microbiol.* (1991) 5(2), pp. 361–366; J. Mengaud et al., *Mol. Microbiol.* (1991) 5(2), pp. 367–372 and Goldfine et al., *Infection and Immunity* (1992) 60(10), pp. 4059–4067). It is likewise known that it is possible to identify these two pathogenic species by means of indirect methods (Notermans et al., *App. and Env. Microbiology* (1991), Vol. 57 No. 9, pp. 2666–2670). According to the method proposed by Notermans et al., the strain of Listeria to be tested, which has previously been isolated, is inoculated as a spot onto the surface of a TY (tryptone yeast extract) agar. After 24 to 48 hours' incubation at 37° C., a second agar layer is poured into the Petri dishes. This second layer contains agarose, chloramphenicol and L-α-phosphatidylinositol, the natural substrate of PIPLC. The dishes are then incubated again at 37° C. and observed for 5 days. This method thus requires several steps, such as the isolation of the strain, the inoculation as a spot onto agar and the distribution of a second layer of agar containing the PIPLC substrate. In addition, this method does not allow *Listeria monocytogenes* bacteria, which are pathogenic for man, or *Listeria ivanovii* bacteria to be distinguished which, as indicated previously, are not pathogenic for man.

The subject of the invention is a medium allowing the identification of pathogenic bacteria of the genus Listeria in a single step.

The present invention relates more especially to a specific culture medium allowing the investigation, the isolation, the counting and the direct identification of pathogenic species of the genus Listeria, the said medium containing a synthetic chromogenic substrate specifically cleaved by PIPLC, especially 5-bromo-4-chloro-3-indolylphosphatidyl-myoinositol. This chromogenic substrate is preferably used in salt form, for example in sodium, potassium or ammonium salt form. Among the salts preferred is ammonium 5-bromo-4-chloro-3-indolylmyoinositol-1-yl-phosphate.

The medium according to the invention allows direct distinction between, on the one hand, *Listeria monocytogenes* and *Listeria ivanovii* which form coloured colonies and, on the other hand, the other species of Listeria whose colonies are not coloured.

According to a preferred method of carrying out the invention, the use of 5-bromo-4-chloro-3-indolyl-phosphatidylmyoinositol allows the detection of the species *Listeria monocytogenes* and *Listeria ivanovii* which form blue colonies, the other species of Listeria remaining non-coloured.

Preferentially, the nutritive agar culture medium according to the invention contains 5-bromo-4-chloro-3-indolylphosphatidylmyoinositol in free form or in salt form, at a concentration of 100 to 500 mg/l, preferably at a concentration of 150 to 300 mg/l.

The nutritive agar culture medium used in the invention must allow the growth of Listeria spp. It is, for example, possible to use Columbia agar, made up of peptones, starch, sodium chloride and agar and well known to the person skilled in the art.

The present invention also relates to the use of 5-bromo-4-chloro-3-indolylphosphatidylmyoinositol or one of its salts for the preparation of a specific culture medium allowing the investigation, the isolation, the counting and the direct identification of pathogenic species of the genus Listeria and especially of the bacterium *Listeria monocytogenes*.

Surprisingly, it has also been found that the addition of blood or of its derivatives, such as, for example, plasma or serum, to the culture medium allows positive PIPLC colonies having a very clear colour to be obtained.

The present invention likewise relates to a specific nutritive agar culture medium, allowing the investigation, the isolation, the counting and the direct identification of pathogenic species of the genus Listeria and especially of the bacterium *Listeria monocytogenes*, said medium containing 5-bromo-4-chloro-3-indolylphosphatidylmyoinositol or one of its salts and blood or one of its derivatives, preferably serum.

The proportion of blood or of its constituents in the medium according to the invention can be between 20 and 80 ml, more especially between 40 and 60 ml, preferably 50 ml per liter of culture medium. Culture media are preferred comprising 5-bromo-4-chloro-3-indolylphosphatidylmyoinositol or one of its salts at a concentration of 100 to 200 mg/ml and serum in a proportion of 40 to 60 ml per liter of medium.

The addition to the culture medium of a pulverulent agent such as kaolin or silica contributes in intensifying the positive colouration of cultures of colonies of PIPLC, thus making the test easier to interpret.

Preferably, the pulverulent agent is added to the culture medium made up with serum.

Nutritive agar culture media according to the invention containing 5-bromo-4-chloro-3-indolylphosphatidylmyoinositol or one of its salts as synthetic chromogenic substrate specifically cleaved by PIPLC, serum and a pulverulent agent, such as kaolin or silica, are also part of the invention.

The concentration of the pulverulent agent in the nutritive agar culture medium depends on the nature of the agent used and can vary between 5 and 30 g/l, preferably between 15 and 25 g/l.

According to the invention, the culture medium can likewise contain a carbohydrate which can be metabolized by *Listeria ivanovii* but not by *Listeria monocytogenes*, such as xylose, for example. The addition of such a carbohydrate to a culture medium containing 5-bromo-4-chloro-3-indolylphosphatidylmyoinositol or one of its salts thus allows the distinction between, on the one hand, *Listeria monocytogenes*, which forms pure blue colonies, and on the other hand, *Listeria ivanovii*, which forms pale blue to green colonies and finally the other species of Listeria whose colonies are uncoloured. Some carbohydrates metabolized by *Listeria monocytogenes* are described in the Manual of Clinical Microbiology (6th Edition—1995) ASM Press Washington D.C. pp. 343–344.

The present invention likewise relates to a specific nutritive agar culture medium allowing the investigation, the isolation, the counting and the direct identification of *Listeria monocytogenes*, the said medium containing 5-bromo-4-chloro-3-indolyl-phosphatidylmyoinositol or one of its salts as synthetic chromogenic substrate specifically cleaved by PIPLC, blood derivatives, preferably serum, a pulverulent agent such as kaolin or silica and a carbohydrate which can be metabolized or fermented by *Listeria ivanovii*, but not by *Listeria monocytogenes*, preferably xylose.

The concentration of the carbohydrate which can be metabolized by *Listeria ivanovii*, but not by *Listeria monocytogenes*, in the culture medium can vary between 5 and 15 g/l and depends, of course, on the carbohydrate used.

The culture medium according to the invention can likewise contain a pH indicator. As pH indicators, it is possible to mention those which are currently used in microbiology, for example alizarinsulphonic acid, Methyl Red, Chlorophenol Red, litmus, Bromocresol Purple, Bromophenol Red, Bromoxylenol Blue, alizarin, Bromothymol Blue, Phenol Red, etc. Of course, the pH indicator must be used in the culture medium in an adjusted concentration. The latter depends on the nature of the indicator and can vary between 50 and 300 mg/l. Among the different pH indicators, it is preferred to use Phenol Red. This indicator even improves the distinction between *Listeria monocytogenes* and *Listeria ivanovii*, the colonies being, when the medium contains 5-bromo-4-chloro-3-indolylphosphatidylmyoinositol or one of its salts, respectively of pure blue colour without colour change of the indicator for *Listeria monocytogenes* and of pale blue colour and surrounded by a yellow circle for *Listeria ivanovii*, this phenomenon being connected with the colour change of the indicator.

According to the invention, a preferred culture medium is a nutritive agar culture medium containing 5-bromo-4-chloro-3-indolylphosphatidylmyoinositol or one of its salts, blood derivatives, preferably serum, a pulverulent agent such as kaolin or silica, a carbohydrate which can be metabolized by *Listeria ivanovii* but not by *Listeria monocytogenes*, preferably xylose, and a pH indicator such as Phenol Red.

On the other hand, the PIPLC activity is not exclusively present in *Listeria monocytogenes* and *Listeria ivanovii*. This enzymatic activity is especially encountered in certain species of Bacillus (Griffith et al., *Methods Enzymol*. (1991) 197, pp. 493–502) and of Clostridium (Taguchi et al., *Arch. Biochem. Biophys*. (1978), 186, pp. 196–201). In addition, the development of a significant saprophytic flora (bacteria or yeasts) on the culture medium can be harmful to the detection of *Listeria monocytogenes* by a competition phenomenon. Thus, it is desirable to inhibit the growth of interfering microorganisms in order to eliminate the risks of false positives (blue colonies formed by bacteria other than *Listeria monocytogenes*) or of false negatives (masking of the blue colouration of the colonizes of *Listeria monocytogenes* by a significant development of other contaminants). To avoid these phenomena, it is recommended to make up the culture medium with antibacterial and/or antifungal agents with respect to which the Listeria spp. are not very sensitive or insensitive. These agents can be used alone or in combination. Among these agents, it is possible to mention, for example, lithium chloride, acriflavine hydrochloride, nalidixic acid, polymixin B, cefotan, colistin sulphate, fosfomycin, ceftazidime, moxalactam, cycloheximide and amphotericin B.

The nutritive agar culture media containing 5-bromo-4-chloro-3-indolylphosphatidylmyoinositol or one of its salts, blood derivatives, preferably serum, a pulverulent agent such as kaolin or silica, a carbohydrate which can be metabolized by *Listeria ivanovii* but not by *Listeria monocytogenes*, preferably xylose, a pH indicator such as, especially, Phenol Red, and antibacterial or antifungal agents are likewise part of the present invention.

The present invention also relates to a method for identification of the pathogenic bacteria of the genus Listeria, comprising:

the inoculation of a sample liable to contain the said pathogenic bacteria of the genus Listeria onto an agar culture medium containing a specific chromogenic substrate of PIPLC, the incubation of said inoculated culture medium with said sample, and the determination of the presence of said pathogenic bacteria of the genus Listeria by the characteristic colour of the substrate. Said sample liable to contain pathogenic bacteria of the genus Listeria is inoculated in a crude form or is previously diluted or is previously concentrated before being inoculated onto a culture medium, such as defined above.

According to a preferred embodiment of the invention, a crude sample to be tested, which is diluted or has been subjected to one or more concentration phases on a nutritive agar culture medium which contains a synthetic chromogenic substrate specifically cleaved by PIPLC, which is 5-bromo-4-chloro-3-indolylphosphatidylmyoinositol or one of its salts, blood derivatives such as serum, a pulverulent agent such as kaolin or silica, a carbohydrate which can be metabolized by *Listeria ivanovii* but not by *Listeria monocytogenes*, preferably xylose and possibly a pH indicator such as, especially, Phenol Red and antibacterial or antifungal agents, is cultured. The presence of *Listeria monocytogenes* is determined by the characteristic colour of its colonies.

The following examples are given in a non-limiting manner to illustrate the invention.

EXAMPLE 1

Differentiation Between Listeria Pathogens, Other Listeria spp. and Interfering Substances.

| PREPARATION OF THE CULTURE MEDIA | |
|---|---|
| Medium 1: base medium | |
| Columbia agar | 39 g/l |
| Lithium chloride | 10 g/l |
| Ceftazidime* | 20 mg/l |
| Moxalactam* | 20 mg/l |
| Polymixin B* | 20 mg/l |
| Amphotericin B* | 3 mg/l |

*thermolabile components

Medium 2: base medium+5-bromo-4-chloro-3-indolyl-phosphatidylmyoinositol

The composition in grams per liter of this medium is identical to that of the medium 1, but the medium 2 additionally contains 300 mg/L of 5-bromo-4-chloro-3-indolylphosphatidylmyoinositol, in ammonium salt form (B-7404 5-bromo-4-chloro-3-indoxylmyoinosi-tol-1-ylphosphate ammonium salt, Biosynth Switzerland).

The preparation of each medium is carried out as follows:

Dissolution of the non-thermolabile components in osmosed water.

Heating of the mixtures to boiling.

Adjustment, if necessary, of the pH to 7.3+/−0.2.

Distribution into flasks at a rate of 95 ml/flask.

Autoclaving of the flasks at 120° C. for 15 minutes.

Addition of the thermolabile components in sterile solution after cooling of the agar to approximately 47° C.

Distribution of the autoclaved media into sterile Petri dishes (diameter 90 mm) at a rate of 15 to 20 ml/dish.

STRAINS TESTED

The strains tested are the following:
Listeria spp.:
*Listeria monocytogenes*
*Listeria ivanovii*
*Listeria innocua*
*Listeria seeligeri*
*Listeria welshimeri*
Interfering substances:
*Bacillus cereus*
*Staphylococcus aureus*
*Candida tropicalis*

CULTURING—INCUBATION—READING

The strains are subcultured in trypto-casein-soya broths and then incubated at 37° C.

After incubation for 18 hours, the broths are diluted in "tryptone salt" diluent, made up of tryptone peptone at 1/100 and sodium chloride at 8.5/1000; so as to obtain suspensions of between $10^6$ and $10^7$ cells/ml.

For each suspension, inoculation is carried out by isolation with a sterile loop of 1 μl, a dish of medium 1 and a dish of medium 2. The dishes are incubated at 37° C. After incubation for 24 hours and 48 hours, the dishes are read. Reading consists in an observation of the colour of the colonies formed by each of the strains in each of the media. The results obtained are indicated in Table I.

TABLE I

| | COLOUR OF THE COLONIES | | | | | | Distinction |
|---|---|---|---|---|---|---|---|
| | path. Listeria | | Non-pathogenic Listeria | | | | path. and non-path. |
| MEDIUM | L.monoc. | L.ivan. | L.inn. | L.seel. | L.welsh | Interfering substances | Listeria |
| 1 | white | white | white | white | white | inhibition | impossible |
| 2 | blue | blue | white | white | white | inhibition | possible |

Medium 2 allows pathogenic and non-pathogenic Listeria species to be differentiated. In addition, the selective supplement allows the bacteria *Bacillus cereus* and *Staphylococcus aureus*, potentially false positives in the culture medium, to be inhibited.

EXAMPLE 2

Differentiation Between Pathogenic Listeria Species and Other Listeria Species

PREPARTION OF THE CULTURE MEDIA

Medium 2: base medium+5-bromo-4-chloro-3-indolyl-phosphatidylmyoinositol

Medium 2 is as described in Example 1.

Medium 3: base medium+5-bromo-4-chloro-3-indolyl-phosphatidylmyoinositol

The composition of medium 3 is identical to that of medium 2 indicated above, but this medium contains 150 mg/l of 5-bromo-4-chloro-3-indolylphosphatidylmyoinositol in ammonium salt form instead of 300 mg/l (medium 2).

Medium 4: base medium+5-bromo-4-chloro-3-indolyl-phosphatidylmyoinositol+blood

The composition of medium 4 is identical to that of medium 3, but this medium additionally contains 50 ml/l of horse blood. For the preparation of the medium, the blood is treated as a thermolabile component.

Medium 5: base medium+5-bromo-4-chloro-3-indolyl-phosphatidylmyoinositol+serum

The composition of medium 5 is identical to that of medium 4, but this medium contains 50 ml/l of horse serum instead of blood.

Medium 6: base medium+5-bromo-4-chloro-3-indolyl-phosphatidylmyoinositol+serum+silica The composition of medium 6 is identical to that of medium 5, but this medium additionally contains 20 g/l of silica, a non-thermolabile component.

The preparation of each medium is carried out as described in Example 1.

STRAINS TESTED

The strains tested are the following:

Listeria spp.:

*Listeeria monocytogenes*

*Listeria ivanovii*

*Listeria innocua*

*Listeria seeligeri*

*Listeria welshimeri*

CULTURING—INCUBATION—READING

For culturing, incubation and reading, the method was as described in Example 1. The results obtained are indicated in Table II.

5-bromo-4-chloro-3-indolyl-phosphatidylmyoinositol in the culture medium to be reduced very significantly.

EXAMPLE 3

Differentiation Between *Listeria monocytogenes* and Other Listeria Species Including *Listeria ivanovii*

PREPARATION OF THE CULTURE MEDIA

Medium 6: base medium+5-bromo-4-chloro-3-indolyl-phosphatidylmyoinositol+serum+silica Medium 6 is as described in Example 2.

Medium 7: base medium+5-bromo-4-chloro-3-indolyl-phosphatidylmyoinositol+serum+silica+xylose The composition of medium 7 is identical to that of medium 6, described in this example, but this medium additionally contains 10 g/l of xylose, a component which for the preparation of the medium is considered as a thermolabile component.

Medium 8: base medium+5-bromo-4-chloro-3-indolyl-phosphatidylmyoinositol+serum+silica+xylose+Phenol Red The composition of medium 8 is identical to that of medium 7 indicated above, but this medium additionally contains 80 mg/l of Phenol Red (non-thermolabile component).

The preparation of each medium is carried out as described in Example 1.

STRAINS TESTED

The strains tested are the following:

Listeria spp.:

TABLE II

| | COLOUR OF THE COLONIES | | | | | Distinction |
|---|---|---|---|---|---|---|
| | pathogenic Listeria | | Non-pathogenic Listeria | | | path. and non-path. |
| MEDIUM | L.monoc. | L.ivan. | L.inn. | L.seel. | L.welsh | Listeria |
| 1 | blue | blue | white | white | White | good |
| 2 | bluish | bluish | white | white | White | average |
| 3 | pure blue | pure blue | white | white | White | excellent |
| 4 | blue | blue | white | white | White | good |
| 5 | pure blue | pure blue | white | white | White | excellent |

The results of Table II demonstrate that in order to carry out a certain and precise reading of the test, that is to say to obtain a good distinction between the pathogenic Listeria species and the non-pathogenic Listeria, it is desirable to make up the culture medium with blood, serum or a mixture of serum and silica. The addition to the medium of the blood, the serum or a mixture of serum and silica contributes in strongly intensifying the blue colouration of the positive PIPLC colonies and thus allows the concentration of

*Listeria monocytogenes*

*Listeria ivanovii*

*Listeria innocua*

*Listeria seeligeri*

CULTURING—INCUBATION—READING

For culturing, incubation and reading, the method was as described in Example 1. The results obtained are indicated in Table III.

TABLE III

| | COLOUR OF THE COLONIES | | | | Distinction | Distinction |
|---|---|---|---|---|---|---|
| | Pathogenic Listeria | | Non-pathogenic Listeria | | path. and non-path. | Listeria monoc. and other |
| MEDIUM | L.monoc. | L.ivan. | L.inn. | L.seel. | Listeria | Listeria |
| 1 | pure blue | pure blue | white | White | possible | impossible |
| 2 | pure blue | pale blue to green | white | White | possible | possible |

TABLE III-continued

| | COLOUR OF THE COLONIES | | | | Distinction | Distinction |
| --- | --- | --- | --- | --- | --- | --- |
| | Pathogenic Listeria | | Non-pathogenic Listeria | | path. and non-path. | Listeria monoc. and other |
| MEDIUM | L.monoc. | L.ivan. | L.inn. | L.seel. | Listeria | Listeria |
| 3 | pure blue (−) | pale blue to green (+) | white (−) | White (+) | possible | possible |

(−): no colour change of the coloured indicator, the agar remains red around the colonies
(− xylose strain)
(+): colour change of coloured indicator, yellow circle around the colonies
(+ xylose strain)

The results of Table III demonstrate that the addition of xylose to the culture medium, preferably in combination with Phenol Red, allows distinction between *Listeria monocytogenes* and all the other species of Listeria, in particular *Listeria ivanovii*.

EXAMPLE 4

Carrying Out the Method According to the Invention 214 strains of the genus Listeria supplied by the Listeria Reference Centre (Institut Pasteur Paris) were tested on medium 8.

The strains corresponding to the following species were used:

12 strains of *Listeria innocua*
10 strains of *Listeria seeligeri*
10 strains of *Listeria welshimeri*
10 strains of *Listeria ivanovii*
1 strain of *Listeria gray*
171 strains of *Listeria monocytogenes*

For culturing, incubation and reading, the method was as described in Example 1.

All the strains of *Listeria monocytogenes* were identified, as well as all the strains of *Listeria ivanovii*, and no false positive result was identified.

This experiment demonstrates the specificity and the reliability of the method according to the invention.

What is claimed is:

1. A nutritive agar culture medium allowing the direct identification of pathogenic bacteria of the genus Listeria, said medium containing a synthetic chromogenic substrate specifically cleaved by the phospholipase C specific of phosphatidylinositol (PIPLC).

2. The culture medium according to claim 1, wherein said chromogenic substrate is 5-bromo-4-chloro-3-indolylphosphatidylmyoinositol or salts thereof.

3. The culture medium according to claim 2, wherein the 5-bromo-4-chloro-3-indolylphosphatidylmyoinositol or salts thereof is at a concentration of 100 to 500 mg/l.

4. The culture medium according to claim 1, further comprising blood or blood derivatives.

5. The culture medium according to claim 4, wherein the proportion of blood or blood derivatives is between 20 and 80 ml per liter of culture medium.

6. The culture medium according claim 1, further comprising a pulverulent agent selected from kaolin or silica.

7. The culture medium according to claim 6, wherein the concentration of the pulverulent agent is between 5 and 30 g/l.

8. The culture medium according to claim 1, further comprising a carbohydrate capable of being metabolized by *Listeria ivanovii* but not by *Listeria monocytogenes*.

9. The culture medium according to claim 8, wherein said carbohydrate is capable of being metabolized by *Listeria ivanovii* but not by *Listeria monocytogenes* is xylose.

10. The culture medium according to claim 8, wherein the concentration of said carbohydrate is between 5 and 15 g/l.

11. The culture medium according to claim 1, further comprising a pH indicator.

12. The culture medium according to claim 11, wherein the concentration of said pH indicator is between 50 and 300 mg/l.

13. The culture medium according to claim 1, further comprising one or more antibacterial and/or antifungal agents, selected from the group consisting of lithium chloride, acriflavine hydrochloride, nalidixic acid, polymixin B, cefotan, colistin sulphate, fosfomycin, ceftazidime, moxalactam, cycloheximide and amphotericin B.

14. A method for identification of the pathogenic bacteria of the genus Listeria, comprising:

the inoculation of a sample liable to contain the said pathogenic bacteria of the genus Listeria onto an agar culture medium containing a chromogenic substrate specific of PIPLC according to claim 1, the incubation of said inoculated culture medium with said sample, and the determination of the presence of said pathogenic bacteria of the genus Listeria by the characteristic colour of the substrate.

15. The method according to claim 14 wherein said sample liable to contain pathogenic bacteria is previously concentrated before being inoculated onto a nutritive agar culture medium allowing the direct identification of pathogenic bacteria of the genus Listeria, said medium containing a synthetic chromogenic substrate specifically cleaved by the phospholipase C specific of phosphatidylinositol (PIPLC).

16. A method of using 5-bromo-4-chloro-3-indolylphosphatidylmyoinositol or salts thereof for the preparation of an agar culture medium allowing the investigation, the isolation the counting and the direct identification of the Listeria bacteria.

17. The culture medium according to claim 2, wherein the 5-bromo-4-chloro-3-indolylphosphatidylmyoinositol or salts thereof is present at a concentration of 150 to 300 mg/l.

18. The culture medium according to claim 1, further comprising serum.

19. The culture medium according to claim 4, wherein the proportion of blood or blood derivatives is present between 40 and 60 ml per liter of culture medium.

20. The culture medium according to claim 4, wherein the proportion of blood or blood derivatives is present between 50 ml per liter of culture medium.

21. The culture medium according to claim 6, wherein the concentration of the pulverulent agent is between 15 and 25 g/l.

22. The culture medium according to claim 1, further comprising a Phenol Red pH indicator.

* * * * *